US 7,005,107 B2

(12) United States Patent
Breda

(10) Patent No.: US 7,005,107 B2
(45) Date of Patent: Feb. 28, 2006

(54) APPARATUS FOR DETERMINING THE SPEED OF SEDIMENTATION OF BLOOD AND OTHER PARAMETERS CORRELATED THERETO

(75) Inventor: Enzo Breda, Udine (IT)

(73) Assignee: Sire Analytical Systems Srl, Udine (IT)

( * ) Notice: Subject to any disclaimer, the term of this patent is extended or adjusted under 35 U.S.C. 154(b) by 0 days.

(21) Appl. No.: 10/641,644

(22) Filed: Aug. 14, 2003

(65) Prior Publication Data

US 2004/0059208 A1 Mar. 25, 2004

Related U.S. Application Data

(62) Division of application No. 09/501,118, filed on Feb. 9, 2000, now Pat. No. 6,632,679.

(30) Foreign Application Priority Data

Nov. 8, 1999 (IT) .............................. UD99A0204

(51) Int. Cl.
*G01N 33/00* (2006.01)
*G01N 21/01* (2006.01)

(52) U.S. Cl. ................... 422/73; 422/82.05; 422/82.09
(58) Field of Classification Search ................ 422/73, 422/82.05, 82.09
See application file for complete search history.

(56) References Cited

U.S. PATENT DOCUMENTS

| 4,201,470 | A | | 5/1980 | Ehrly et al. |
| 4,352,557 | A | | 10/1982 | Schmid-Schonbein et al. |
| 4,398,894 | A | * | 8/1983 | Yamamoto ................... 436/517 |
| 4,436,827 | A | * | 3/1984 | Tamagawa ................. 435/7.25 |
| 4,822,568 | A | | 4/1989 | Tomita |
| 5,567,869 | A | | 10/1996 | Hauch et al. |
| 5,827,746 | A | | 10/1998 | Duic |

FOREIGN PATENT DOCUMENTS

EP 0529420 A2 3/1993

* cited by examiner

*Primary Examiner*—Monique T. Cole
(74) *Attorney, Agent, or Firm*—Akin Gump Strauss Hauer & Feld, LLP

(57) ABSTRACT

Method and apparatus to determine the speed of sedimentation of blood and other parameters connected thereto, said method being carried out by detecting the development over time of the optical density, or absorbance, of a sample of blood, said sample being sent in the form of a flow inside a capillary container, said detection being made in correspondence with a point of said capillary container and the relative data acquired being processed to obtain said speed of sedimentation and said connected parameters, said method providing to instantly interrupt the flow of the blood sample flowing inside said capillary container, in order to determine a thickening of the red cells in said blood sample and their consequent sedimentation, said detection being made substantially simultaneously with said instant interruption.

14 Claims, 2 Drawing Sheets

APPARATUS FOR DETERMINING THE SPEED OF SEDIMENTATION OF BLOOD AND OTHER PARAMETERS CORRELATED THERETO

CROSS REFERENCE TO RELATED APPLICATION

This application is a division of U.S. application Ser. No. 09/501,118, filed Feb. 9, 2000 now U.S. Pat. No. 6,632,679, entitled "Method to Determine The Speed of Sedimentation Of Blood and Other Parameters Correlated Thereto, And Relative Apparatus," the entire disclosure of which is incorporated herein by reference.

FIELD OF THE INVENTION

This invention concerns a method and the relative apparatus used, in the field of medical analyses, to determine the speed of sedimentation of blood ("ESR"), and also other parameters correlated thereto, such as viscosity, elasticity, density or otherwise.

BACKGROUND OF THE INVENTION

In the field of medical analyses, to ascertain pathological states defined as inflammatory, the speed of sedimentation of the corpuscular part of the blood is measured, particularly the erythrocytes or red cells.

To establish the ESR, various methods have been adapted but these have not proved to be completely satisfactory, in that detection is neither quick nor practical.

In these methods, which use different measuring systems, the blood taken from the patients is put into tubular containers and subsequently, possibly after centrifuging, the due measurements are made on the blood samples.

Other systems provide to detect, at pre-set intervals of time, the position of the separation interface between the fluid plasma part of the blood, substantially clear, and the corpuscular part consisting of red and white cells and platelets, which is more turbid.

Other systems provide to detect the optical density or absorbance of the blood in correspondence with the separation interface.

Other cases provide to use optothermic sensors suitable to detect at defined intervals the heat produced by the blood sample absorbing radiation which strikes it.

The different methods to determine ESR which have been proposed until now are all characterized by an initial dead time which has a considerable influence on the time required for analysis; the latter cannot therefore be done in succession with other analyses which are much quicker, such as for example blood cell counts.

Conventional methods, moreover, have to use disposable containers, which entails an increase in costs both to purchase them and to dispose of them. Furthermore, the quantity of blood needed to do the analysis is high, and this entails problems in some particular cases, for example when the analysis involves children.

The state of the art also includes a method, proposed by the same Applicant, which provides to withdraw the blood to be analyzed from the container in which it is kept and to introduce the blood into a measuring volume, of limited thickness, which is used for various measurements made on different samples.

This method is based on the detection of the optical density or absorbance of the blood at a fixed point of the measuring volume, which is made to rotate to accelerate the sedimentation of the blood.

The means used to detect the absorbance comprise devices to emit/detect electromagnetic radiations associated with the measuring volume. The absorbance values detected are directly proportional to the number of cells in the blood sample at the point of observation, and this number varies over time due to the effect of the sedimentation of the cells.

By studying the absorbance over time it is possible to obtain the ESR value by eliminating the initial dead times and obviating the need to use disposable containers for the analysis.

Moreover, the quantity of blood needed is less and therefore the analysis can be done without any problems, even on paediatric patients.

Although it has these advantages, the method is also characterized by some problems which prevent it from being used in a completely satisfactory manner.

The size of the apparatus used to measure the ESR and the difficulties involved in managing several centrifugal means limit the possibility of using the system with an integrated instrument for counting the blood cells. Moreover, the size of the apparatus requires the analyses to be made in the laboratory and the method of analysis itself still requires volumes of blood which are in any case considerable.

Furthermore, after every measurement, the centrifugal means and the volume associated therewith always have to be repositioned with respect to the emission/detection means, which creates problems and anomalies in controlling the flow of blood.

In this apparatus, after each test, the blood sample is discharged and a new blood sample is introduced into the measuring volume.

To avoid washing the measuring volume after discharge, the residue of the sample which has already been analyzed is discharged by the new blood sample to be analyzed, since the hydraulic path which the blood has to follow to avoid pollution is rather long; this increases the volume of blood which has to be used.

A further limit of this method is that the acquisition of the photometric data depends on the speed of rotation of the measuring volume and therefore cannot be considered a continuous phenomenon.

The Applicant has devised and embodied this invention to perfect and extend the field of use of the apparatus described above, and also to obtain further advantages.

SUMMARY OF THE INVENTION

The invention is set forth and characterized in the respective main claims, while the dependent claims describe other characteristics of the invention.

The purpose of the invention is to supply a method and the relative apparatus to determine the speed of sedimentation of blood, and other parameters correlated thereto, which will allow a rapid, easy and reliable analysis which can be done in combination with haematological analyses of a different type.

Another essential purpose of the invention is to allow the apparatus to be integrated into existing systems for blood cells counting, thus exploiting the homogenisation of the blood already achieved by said systems.

Another purpose is to achieve a compact apparatus which is easy to transport, practical to use under any conditions and in any environment and which can also be used as an instrument in the ambulatory or hospital.

A further purpose of the invention is to eliminate the need to centrifuge the container and hence all the problems relating to its integration with other devices, controlling the flow, discontinuity of monitoring, etc.

The apparatus to determine ESR according to the invention comprises a capillary container, transparent to the electromagnetic radiations within a certain field of wavelengths, with at least a substantially rectilinear segment and of extremely limited size inside which the blood to be analyzed is introduced.

The apparatus also comprises pump means suitable to send a blood sample inside the capillary, so that the blood sample can be passed through by an electromagnetic radiation emitted by transmission means and detected by mating reception means arranged in correspondence with a point of the capillary container.

The reception means are connected to a processing unit suitable to transform the values detected into an expression of the sedimentation speed, or other parameters correlated thereto, expressed in a unit of measurement compatible with those normally used.

According to the main characteristic of the invention, the pump means are arranged to suddenly interrupt the flow of blood flowing through the capillary, so as to cause a strong deceleration (stopped-flow) and then an aggregation and sedimentation of the blood cells as the blood compacts.

This compaction causes a variation in the signal detected by the detection means with a consequent acquisition of the information used to determine the ESR.

When detection is finished the blood sample analyzed is discharged from the circuit and the capillary is ready to receive a new blood sample to analyze.

Since there are no centrifugal means it is possible to limit the length of the circuit wherein the blood circulates, and also eliminate the discontinuity and joints which create anomalies in the flow and encourage the formation of clots and bubbles.

On the one hand this allows to reduce the bulk of the whole apparatus and on the other hand to limit the quantity of blood needed to clean the capillary and for the analysis.

The configuration of the apparatus described allows it to be greatly reduced in size, and to be integrated in an optimum manner with pre-existing blood cells counting devices; consequently, the sample can be supplied to the capillary already in a condition of optimum homogenization, without the measuring apparatus needing auxiliary instruments for this function.

Moreover, with this apparatus, which requires microvolumes of blood in the order of 1–50 µl, the analysis can be done with optimum results even on samples from children or new-born infants, where very little blood is taken and very small instruments have to be used.

In the apparatus according to the invention, the capillary container, the means to take the blood sample and the optical detection sensor may constitute a transportable structure which is distinct and separate from the processing unit and any optional system to display the results, and can be connected thereto by means of transmission cables or even via radio.

In this way, we obtain a great deal of flexibility and versatility of use, since the sampling and analysis instrument may be small in size and thus can be used, for example, directly from the bed of a patient, or under difficult conditions.

It is also possible to use a plurality of such apparatuses in parallel, to do the same test on different blood samples at the same time, or to use the same apparatus in series with other devices suitable to do different types of blood tests on the same sample.

Due to the very limited time needed for the test, the apparatus can also be used in local ambulatories, wards, mobile blood units or, as already mentioned, integrated with apparatuses suitable for blood tests of another type.

The apparatus allows to analyze the blood continuously and directly, immediately after it has been taken pure from the patient; it does not need anti-coagulants since the blood can be analyzed before the clot has time to form.

The detection means acquire data continuously, which allows a better evaluation of the optical density of the blood sample, and therefore an extremely precise measurement of the ESR; it also allows to detect any possible anomalies in the blood flow, for example due to air bubbles or clots.

The continuous study of the flow can also be used to determine other parameters of the rheology of the blood, such as the density or viscosity.

In a preferential embodiment of the invention, the pump means are reversible and allow to invert the flow inside the circuit; this allows to re-homogenize the blood sample and to rapidly repeat measurements thereof.

The capillary is suitable to be associated with a thermostat to allow analysis to be made at a constant temperature which can be set in advance as desired.

It is thus possible to make the same blood sample transit through capillary containers set at different temperatures and arranged in series, evaluating the ESR values according to the variation in the testing temperature.

In this case, it is preferable that at least one of the capillaries is maintained at a temperature of around 37° C., in order to prevent the precipitation of some components of the blood and to guarantee a reliable control.

BRIEF DESCRIPTION OF THE DRAWINGS

These and other characteristics of the invention will become clear from the following description of a preferential form of embodiment of the invention, given as a non-restrictive example, with reference to the attached drawings wherein.

DETAILED DESCRIPTION OF PREFERRED EMBODIMENT

Figure 1:
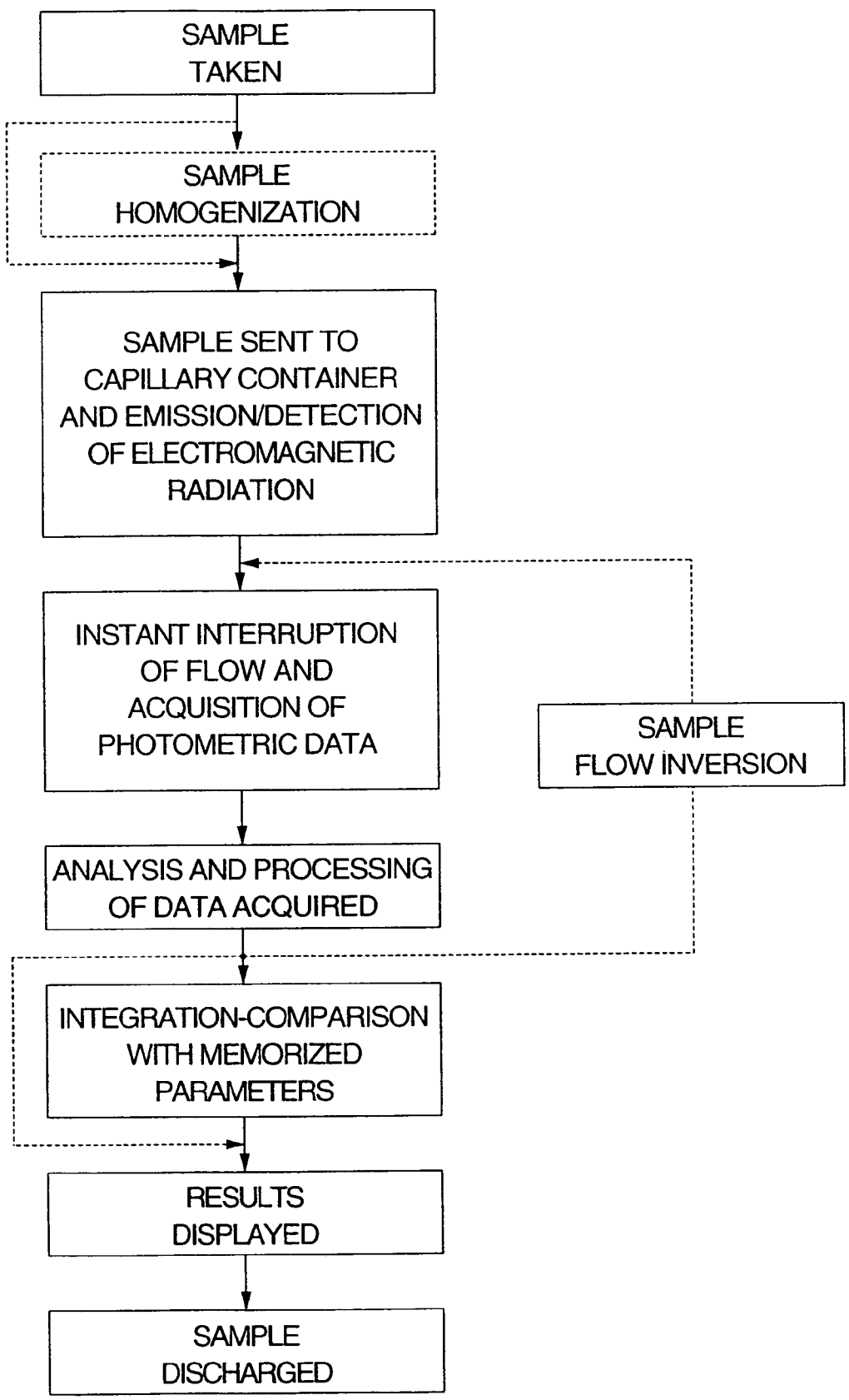
FIG. 1 is a flow diagram of the method to determine the ESR and other parameters according to the invention.
Figure 2:
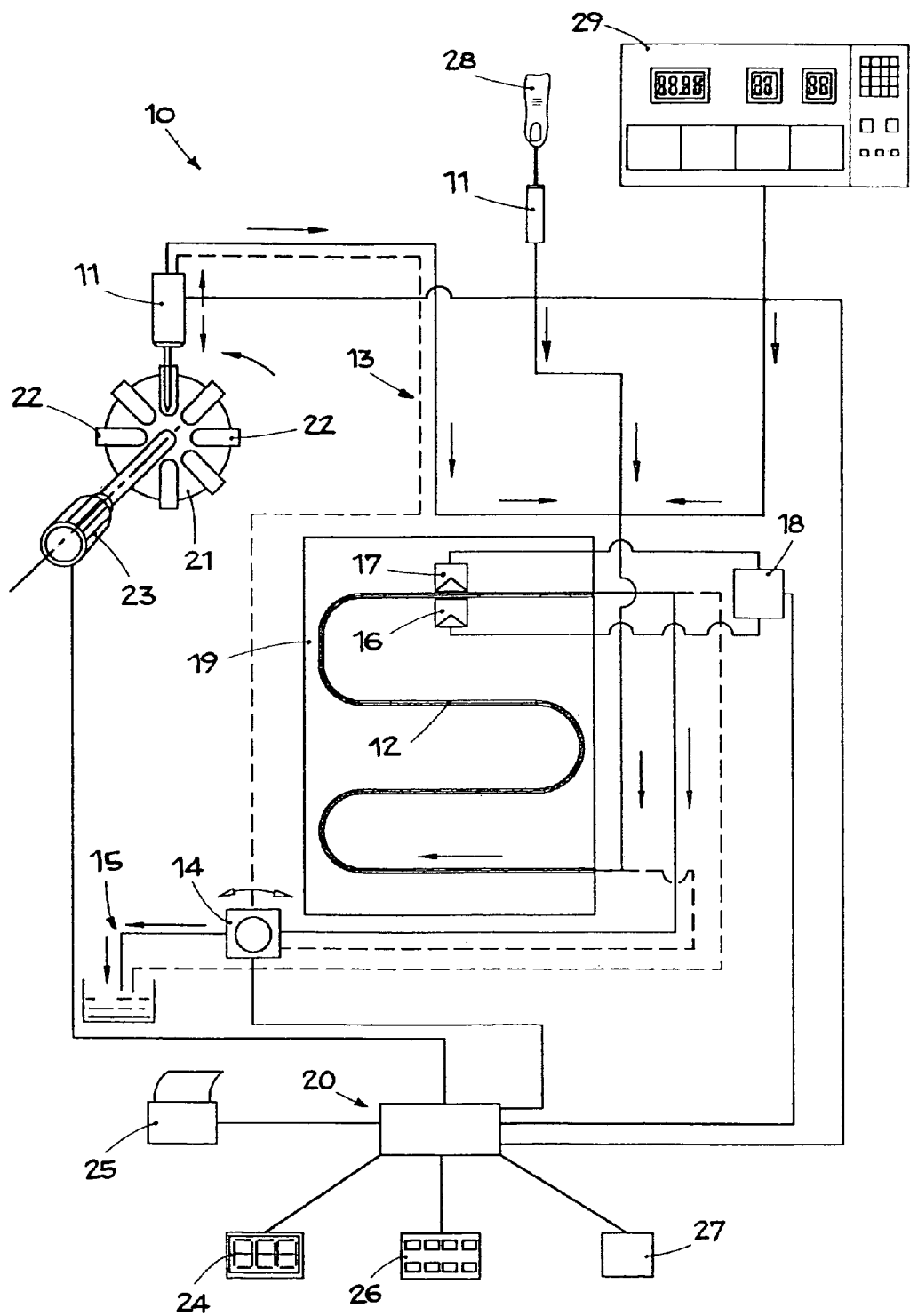
FIG. 2 is a schematic view of the apparatus to determine the speed of sedimentation of blood and other parameters according to the invention.

FIG. 2 shows schematically an apparatus 10 to determine the speed of sedimentation of blood and other parameters connected thereto, which mainly comprises the following components:

- a sample-withdrawing organ 11 to take the blood sample to be analyzed;
- a capillary container 12, transparent to electromagnetic radiations in a field of between 100 and 1500 nm, preferentially between 200 and 1000 nm, inside which the blood sample is suitable to be introduced;
- a circuit 13 which connects the sample-withdrawing organ 11 to the capillary 12 and inside which the blood sample is suitable to circulate;

an instant stoppage pump 14 associated with the circuit 13;

a discharge conduit 15 to discharge the blood sample after analysis;

an optical sensor comprising a device 16 to emit electromagnetic radiations associated with a mating detector device 17, in this case arranged on opposite sides with respect to a particular point of the capillary 12;

a control and processing unit 20 suitable to manage the working of the apparatus 10 and an interface unit 18 by means of which the devices 16 and 17 are connected to the control and processing unit 20.

The sample-withdrawing organ 11, in this case of the syringe type, is suitable to selectively take the blood sample to be analyzed from the containers 22 of a storage drum 21, which can be made to rotate by a motor 23.

According to the variant shown here, the sample-withdrawing organ 11 can also be used to withdraw the blood directly from the finger 28 of a patient, for example with a syringe device of the type with a spring and containing the capillary 12 and the devices 16, 17.

Moreover, the blood may arrive in the capillary 12 from an apparatus 29 able to carry out other tests, inside which the entire apparatus 10 may be integrated; in this way the blood arriving in the capillary 12 is already homogenized and does not require further additional processing.

According to a variant, the sample-withdrawing organ 11 is provided as an integral part with stirrer means to homogenize the blood sample taken.

The capillary container 12 consists of a thin conduit, in this case shaped like a coil, defining an inner measuring cell with a thickness of between 0.1 and 3 mm, advantageously 1 mm.

The capillary 12 is associated with a metal support 19 provided with thermostat means which allow it to be kept at a constant temperature which can be set as desired, conditioning the temperature at which the analysis is done.

The pump 14, which can be arranged either upstream or downstream of the capillary 12, is suitable to activate the sample-withdrawing organ 11 to make the blood sample circulate inside the circuit 13 and the capillary 12; another function is to interrupt the flow of the sample instantly.

In a preferential embodiment, the pump 14 is reversible and suitable to allow the blood to circulate inside the circuit 13 in two directions, indicated respectively with a continuous line (intake) and a line of dashes (thrust).

The emission device 16 and the mating detection device 17 are facing each other and opposite in a segment of the capillary 12; they are suitable respectively to emit and detect electromagnetic radiations with a wavelength advantageously between 200 and 1000 nm.

The interface unit 18 is suitable to activate/de-activate the emission device 16 and to translate the signals received by the detector device 17 into signals which can be read by the control and processing unit 20.

The control and processing unit 20, consisting of an electronic microprocessor, can be programmed to manage various functioning modes of the apparatus 10.

It comprises a data bank or inner memory 27, in which a series of parameters are contained in the form of numerical data, tables or graphs.

The control and processing unit 20 also comprises means to interface with the user, in this case consisting of a keyboard 26 to insert the data, a monitor or display 24 and a printer 25 to display the results of the analysis and to process them for statistical purposes.

The method according to the invention provides to take the blood sample to be analyzed with the sample-withdrawing organ 11 driven by the pump 14.

In the case shown here, the blood sample can be taken from a container 22 housed in a storage drum 21 in the laboratory; alternatively, as explained, the blood sample can be taken directly from the patient, or the blood can arrive in the capillary 12 after being subjected to other types of testing in another apparatus 29, for example a blood cells counter.

Since the testing is done immediately after the blood sample has been taken, there is no need for a step to homogenize the blood.

Subsequently, the blood sample is made to circulate inside the circuit 13 until it reaches the capillary 12, where it is struck by an electromagnetic radiation emitted by the emission device 16 and detected by the detector 17.

The flow of the blood sample is then interrupted by an instant stoppage of the pump 14 commanded by the control and processing unit 20; the considerable deceleration of the flow causes the compaction and subsequent sedimentation of the cells in the blood sample.

At the same time as the pump 14 stops, the control and processing unit 20 commands the detector 17 to acquire the photometric data of optical density or absorbance.

It may take a variable period of time to acquire the data, but may reach very limited values with a minimum in the order of 0.1 seconds; normally, it takes between 1 and 30 seconds.

The data acquired are transmitted in real time to the control and processing unit 20 which memorizes them and processes them to obtain the ESR value and the correlated parameters. The data acquired can be compared or integrated with parameters in the internal memory 27 before being processed to determine the ESR value.

The results of the analysis are then displayed on the display 24 and/or printed by the printer 25 while the blood sample is discharged through the discharge conduit 15.

According to a variant, at the end of the data-acquisition period, the blood sample is made to circulate in the opposite direction inside the circuit 13 and the capillary 12, by inverting the direction of the pump 14.

The flow of blood is then interrupted instantly and a new step is started to acquire the photometric data by the detector 17; these data are then integrated with those acquired before.

According to another variant, the same blood sample is analyzed at different temperatures, varying the thermostat of the metal support 19, or by making the blood sample pass through a plurality of capillaries 12 mounted on metal supports 19 set at different temperatures, which may even be part of the same apparatus 10 and be connected in series.

It is obvious, however, that modifications and additions may be made to the method and apparatus 10 as described heretofore, but these shall remain within the field and scope of this invention.

For example, the emission 16 and detection 17 devices may be positioned on the same side of the capillary container 12 and may detect the reflection of the radiation emitted.

Moreover, the emission device 16 can be arranged to emit polarized light in order to obtain characteristic results according to the type of polarization.

Or the instant stoppage of the flow of blood may be achieved by valve means associated with the circuit 13 and/or the capillary container 12.

It is also obvious that, although the invention has been described with reference to specific examples, a person skilled in the art shall be able to supply many other equivalent versions of the method to determine the speed of sedimentation of blood and achieve analogous forms of the relative apparatus, but these shall all come within the field and scope of the invention.

I claim:

1. An apparatus for determining the speed of sedimentation, viscosity, elasticity, and density of blood by detecting the development over time of an optical density, or an absorbance, of a sample of blood, the apparatus comprising:
   a blood sample-withdrawing organ;
   a capillary container inside which the sample of blood is flowable;
   a circuit connecting the blood sample-withdrawing organ with the capillary container;
   a sensor in optical communication with the capillary container, the sensor configured to determine the optical density, or the absorbance, associated with the sample of blood when the sample of blood is in the capillary container;
   a processing unit associated with the sensor and having an inner memory, the processing unit configured to acquire photometric data of the optical density, or the absorbance, associated with the sample of blood, and to compare the photometric data with reference parameters contained in the inner memory to determine the speed of sedimentation, viscosity, elasticity and density of the blood sample;
   a pump in fluid communication with the circuit, the pump configured to circulate the sample of blood inside the circuit and the capillary container; and
   a stop operatively coupled to the pump, the stop configured to control the operation of the pump to instantly interrupt the circulation of the sample of blood at least inside the capillary container.

2. The apparatus of claim 1 wherein the stop is electrically coupled to the pump.

3. The apparatus of claim 1 wherein the stop comprises at least one valve in fluid communication with the circuit or the capillary container.

4. The apparatus of claim 1 wherein the capillary container has a thickness of between 0.1 and 3 mm in at least a detection segment.

5. The apparatus of claim 1 wherein said capillary container is transparent to electromagnetic radiations in a range of wavelengths between 200 and 1000 nm.

6. The apparatus of claim 1 wherein the sensor includes an emission device and an electromagnetic wave detector arranged in cooperation with the capillary container, and a processing unit configured at least to activate and de-activate the emission device and to convert a signal supplied by the detector.

7. The apparatus of claim 6 wherein the blood sample-withdrawing organ, emission device and detector are positioned in a small, autonomous, transportable unit, and are connected to the processing unit by transmission cables or by radio frequency signal.

8. The apparatus of claim 1 configured for integration into a system configured to perform a plurality of tests on the sample of blood, the plurality of tests including counting a number of blood cells.

9. The apparatus of claim 1 wherein the pump is reversible and is configured to act selectively in suction or in thrust on the sample of blood, thereby capable of causing an inversion of flow of the sample of blood inside the circuit and the capillary container.

10. The apparatus of claim 1 wherein the capillary container is associated with a support, a temperature of the support being settable by a thermostat in a variable manner.

11. The apparatus of claim 10 further comprising a plurality of capillary containers connected in series, each capillary container associated with a respective support settable to a different temperature by a thermostat.

12. The apparatus of claim 1 wherein the blood sample-withdrawing organ includes a manually-activated syringe.

13. The apparatus of claim 1 wherein the blood sample-withdrawing organ cooperates with a blood storage drum.

14. The apparatus of claim 1 wherein the blood sample-withdrawing organ cooperates directly with a finger of a patient to receive at least a drop of blood to be analyzed.

* * * * *